United States Patent [19]

Kin et al.

[11] Patent Number: 5,055,615
[45] Date of Patent: Oct. 8, 1991

[54] SQUARIUM COMPOUNDS, A PROCESS FOR PREPARING THEM AND ELECTROPHOTOGRAPHIC PHOTORECEPTORS CONTAINING THEM

[75] Inventors: Seki Kin; Hiroyuki Tanaka; Satoshi Saeki; Kaoru Torikoshi; Lyong S. Pu, all of Kanagawa, Japan

[73] Assignee: Fuji Xerox Co., Ltd., Tokyo, Japan

[21] Appl. No.: 233,101

[22] Filed: Aug. 17, 1988

Related U.S. Application Data

[60] Division of Ser. No. 26,598, Mar. 17, 1987, abandoned, which is a continuation of Ser. No. 733,166, May 13, 1985, abandoned.

[30] Foreign Application Priority Data

May 11, 1984 [JP] Japan .................................. 59-92765
May 11, 1984 [JP] Japan .................................. 59-92770

[51] Int. Cl.$^5$ ............................................. C07C 85/00
[52] U.S. Cl. ........................................ 564/307; 430/74; 558/410; 558/418; 558/419; 560/451; 562/457
[58] Field of Search ............................ 564/307; 430/74; 558/416, 419, 418; 560/45; 562/457

[56] References Cited

U.S. PATENT DOCUMENTS

| | | | |
|---|---|---|---|
| 4,521,621 | 6/1985 | Yanus et al. | 564/307 |
| 4,523,035 | 6/1985 | Yanus et al. | 564/307 |
| 4,524,220 | 6/1985 | Law | 564/307 |
| 4,525,592 | 6/1985 | Law et al. | 564/307 |
| 4,552,822 | 11/1985 | Kazmaier et al. | 564/307 |
| 4,621,038 | 11/1986 | Kazmaier et al. | 564/307 |
| 4,624,904 | 11/1986 | Kazmaier et al. | 564/307 |
| 4,644,082 | 2/1987 | Law et al. | 564/307 |
| 4,746,756 | 5/1988 | Kazmaier | 564/307 |

OTHER PUBLICATIONS

Kin et al., Chem. Abs. vol. 105, No. 8, entry #70134g (1986).
Tubegawa et al., Chem. Abs. vol. 105, No. 16, entry #143544c (1986).
Law et al., Chem. Abs. vol. 108, No. 18, entry #152134h (1988).
Akasaki et al., Chem. Abs. vol. 108, No. 22, entry #195928p (1988).
Ahasaki et al., Chem Abs. vol. 108, No. 22, entry #195929p (1988).
Ahasaki et al., Chem. Abs. vol. 108, No. 22, entry #195930g (1988).
Ahasaki et al., Chem. Abs. vol. 108, No. 22, entry #195932 (1988).
Ahasaki et al., Chem Abs. vol. 109, No. 20, entry #180416r (1988).

*Primary Examiner*—Mukund J. Shah
*Assistant Examiner*—E. C. Ward
*Attorney, Agent, or Firm*—Sughrue, Mion, Zinn Macpeak & Seas

[57] ABSTRACT

Novel squarium compounds which have a flat photosensitivity in the wide range from the visible ray region to the near infrared ray region as a charge generator and which can be prepared by reacting squaric acid and an aniline derivative, and electrophotographic photoreceptors containing them are provided.

1 Claim, 1 Drawing Sheet

SQUARIUM COMPOUNDS, A PROCESS FOR PREPARING THEM AND ELECTROPHOTOGRAPHIC PHOTORECEPTORS CONTAINING THEM

This is a division of application Ser. No. 07/026,598 filed Mar. 17, 1987, which is a continuation of application Ser. No. 06/733,166 filed May 13, 1985, both now abandoned.

FIELD OF THE INVENTION

This invention relates to novel squarium compounds having a flat photosensitivity in the wide range from the visible ray region to the near infrared ray region useful as a charge generator, a process for preparing them and electrophotographic photoreceptors containing them.

BACKGROUND OF THE INVENTION

Up to now, as electrophotographic photoreceptors, inorganic photosensitive materials such as amorphous selenium, selenium alloys, cadmium sulfide and zinc oxide and organic photosensitive materials represented by polyvinylcarbazole and polyvinylcarbazole derivatives have been widely known.

It is common knowledge that amorphous selenium or selenium alloys have superior characteristics and have been put into practical use. However, a complicated vacuum metallizing or deposition process is necessary for their production and further the vacuum-deposited film obtained has a drawback in that it lacks flexibility. Zinc oxide is used as a dispersed photosensitive material in which zinc oxide is dispersed in a resin, but it is disadvantageous in that the resulting photographic material has unsatisfactory mechanical strength and cannot be used repeatedly as is.

Polyvinylcarbazoles, well known as organic photoconductive materials, are advantages in that they have transparency, processability and film-formability. However, they have no photosensitivity in themselves in the visible ray region, and cannot be used practically as is. Accordingly, various sensitization methods have been provided. The spectral sensitization of polyvinylcarbazole using a sensitizing dye can expand its spectral sensitivity to the visible ray region. However, a sufficient photosensitivity for use as a electrophotographic photoreceptor is not obtained, and they have a drawback in that photo-fatique is remarkable.

On the other hand, spectral sensitization with an electron acceptor gives rise to electrophotographic photoreceptors having sufficient photosensitivity, and some of them have been practically used. However, there are still some problems with mechanical strength and durability.

Extensive research has been conducted on organic dispersed photosensitive materials, and there are many reports. However, electrophotographic photo-receptors having a superior electric characteristic and a sufficient photosensitivity have not been obtained yet. At present, there are reports about phthalocyanines which show superior electrophotographic characteristics for use as dispersed photosensitive materials. However, their spectral sensitivity is partial to the long wavelength region, and they have a drawback in that reproduction of red color is inferior.

SUMMARY OF THE INVENTION

An object of this invention is to provide novel squarium compounds having a flat photosensitivity in the wide range from the visible ray region to the near infrared ray region, a process for preparing them and electro-photographic photoreceptors containing them.

Another object of this invention is to provide photoconductive materials having high photographic sensitivity, which can be used in every electrophotographic process and have a spectral sensitivity in the range from the visible ray region to the near infrared ray region.

A further object of this invention is to provide electrophotographic photoreceptors which have a flexibility that inorganic photosensitive materials fail to have, which are free from drawbacks of organic photosensitive materials such as polyvinylcarbazole-trinitrofluorenones, that is, a low abrasion resistance and lack of mechanical strength and which are superior in mechanical strength such as abrasion resistance and have a flat spectral sensitivity in the wide range from the visible ray region to the near infrared ray region.

Extensive research has been conducted in order to obtain photoconductive materials which overcome drawbacks of conventional inorganic photosensitive materials, organic photosensitive materials or organic dispersed photo-sensitive materials, which have both superior electro-photographic characteristics and processability, and further which have high photosensitivity in the wide range from the visible ray region to the near infrared ray region. As a result, it has now been found that the squarium compounds represented by the following general formula (I) possess extremely superior characteristics, and this invention has been completed based on the discovery.

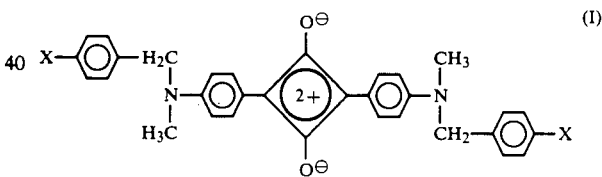

wherein X represents a nitro group, a cyano group, a carboxyl group or an ethoxycarbonyl group.

DETAILED DESCRIPTION OF THE INVENTION

The squarium compounds of this invention represented by general formula (I) above can be prepared by reacting 3,4-dihydroxy-3-cycloacetene-1,2-dione (hereinafter referred to as "squaric acid") represented by the following formula (II):

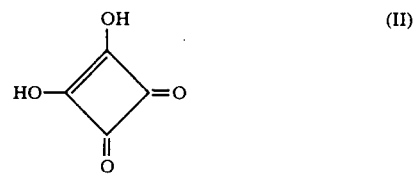

with an aniline derivative represented by general formula (III):

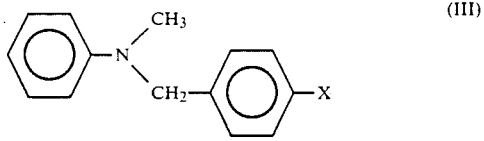

wherein X has the same meaning as above.

The reaction of squaric acid represented by formula (II) with an aniline derivative represented by general formula (III) can be carried out by heating squaric acid and an aniline derivative in an inert organic solvent such as n-butyl alcohol or amyl alcohol at about 100° to about 140° C. for about 3 hours to about 5 hours. The resulting compound can be purified by washing the compound obtained and then recrystallizing the compound from a suitable solvent to give the desired compound.

Examples of the squarium compounds of this invention represented by general formula (I) above include the following compounds.

Compound (1):

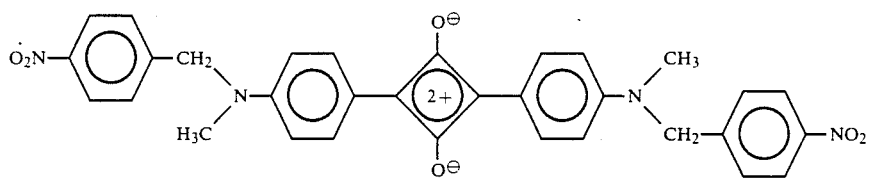

Compound (2):

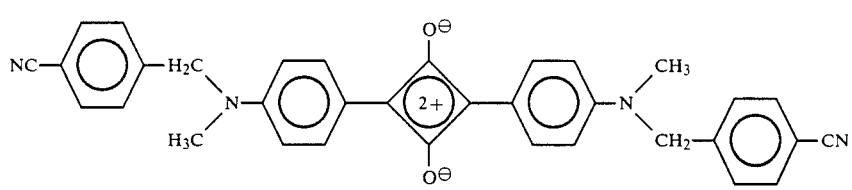

Compound (3):

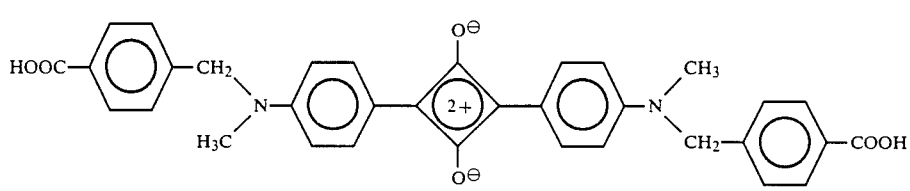

Compound (4):

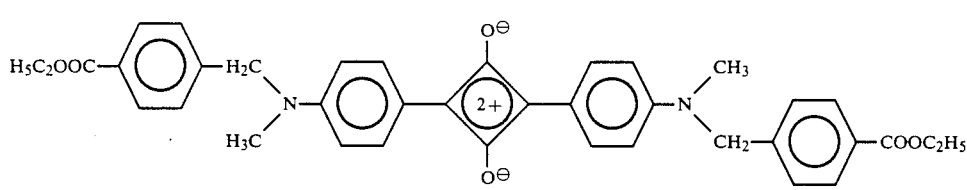

The spectral sensitivity of the squarium compounds of this invention show a flat photosensitivity in the range from 400 to 850 nm, and the squarium compounds of this invention have a sufficient photosensitivity in the range from all the visible ray region to the near infrared ray region.

The squarium compounds represented by general formula (I) can be used in electrophotographic photoreceptors having a multilayer structure. That is, in electrophotographic photoreceptors having a double layer structure consisting of a charge generation layer and a charge transport layer, a combination of the charge generation layer containing a squarium compound of this invention and a known charge transport layer comprising a binder resin containing a photoconductive polymer (such as polyvinyldibenzothiophene, a polyvinylpyrene, a polyvinylanthracene and a polyvinylcarbazole) or a photoconductive compound (such as triarylpyrazoline, triphenylmethane, oxadiazole, tetraphenylbenzidine, and trinitrofuluorenone) results in the improvement of chargeability of electrophotographic photo-receptors, lowering of residual potential, and further the improvement of mechanical strength.

Figure 1:
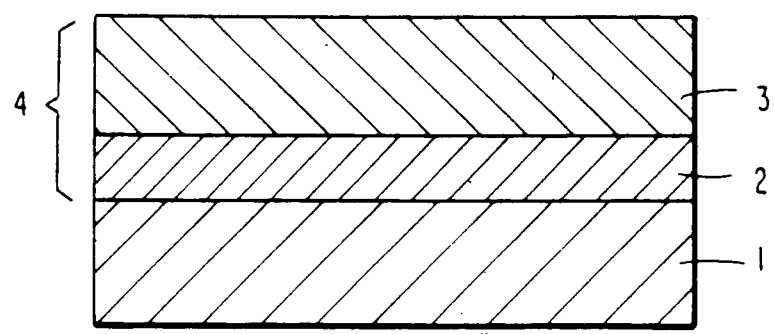
FIGS. 1 and 2 are profile sections of compositions of electrophotographic photoreceptors of this invention.
Figure 2:
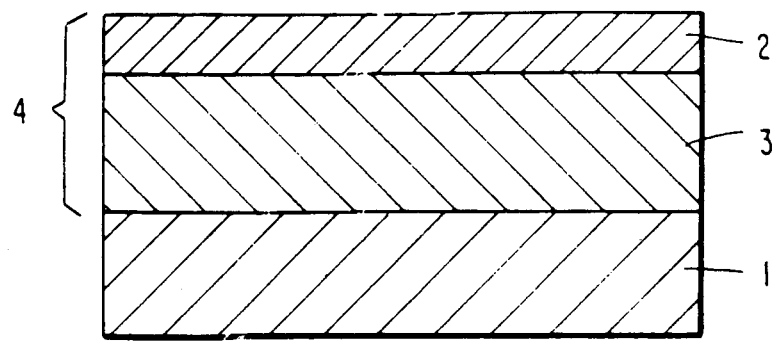

As shown in FIGS. 1 and 2 which illustrate the construction of electrophotographic photoreceptors of this invention having a double layer structure, a photo-sensitive layer 4 composed of a lamination of a charge generation layer 2 containing a squarium compound of this invention and a charge transport layer 3 containing a charge transport material is provided on an electroconductive support 1. The thickness ratio of the charge generation layer to the charge transport layer is preferably from about ½ to about 1/200. Further, the squarium compound and a charge transport material may be incorporated into one layer to form a single-layered photoreceptor, if desired.

The charge generation layer can consist of a squarium compound alone or a combination of the squarium compound and a binder resin. The ratio of the squarium compound represented by general formula (I) to the binder resin used is from about 10% by weight to about 90% by weight, preferably from about 10% by weight to about 50% by weight.

There is a solvent coating method and a vacuum deposition method for preparing the charge generation layer using the squarium compound of this invention without use of a binder resin.

The film thickness of the charge generation layer is from about 0.1 to about 3 μm, preferably from about 0.2 to about 1 μm.

For the purpose of its dispersion in a binder, the squarium compound may be ground into fine particles by a known method using any conventional mill, such as an SPEX MILL, ball mill or RED DEVIL (trade name). Particle size of the pigment is generally not more than 5 μm, preferably from 0.01 to 3 μm, but the particle size is not limited thereto.

The binder used in the charge generation layer may have or may not have a photoconductivity. Examples of the binders having photoconductivity include photoconductive polymers such as polyvinylcarbazoles, polyvinylcarbazole derivatives, polyvinylnaphthalenes, polyvinylanthracenes., polyvinylpyrenes, or other organic matrix materials having a charge transport property.

Moreover, known insulating resins having no photoconductivity can be used as a binder.

Examples of the known insulating resins include polystyrenes, polyesters, polyvinyltoluenes, polyvinylanisoles, polychlorostyrenes, polyvinyl butyrals, polyvinyl acetates, polyvinyl butylmethacrylates, copolystyrenebutadienes, polysulfones, copolystyrene-methyl methacrylates and polycarbonates.

In order to improve the mechanical strength of the electrophotographic photoreceptors obtained, a plasticizer can be used as in the case of ordinary polymeric materials.

Examples of the plasticizer include a chlorinated paraffin, a chlorinated biphenyl, a phosphate plasticizer and a phthalate plasticizer. By the addition of 0 to 10% by weight of the plasticizer based on the weight of the binder, the mechanical strength of the electrophotographic photoreceptor is further improved without lowering of photosensitivity and electrical characteristics.

The binder having dispersed therein a squarium compound of the present invention is coated on an electroconductive support.

As a coating method, a dip coating method, a spray coating method, a bar coater method and an applicator method can be employed. A good photosensitive layer can be obtained by every method above.

Usable electrically conductive supports include metals (e.g., aluminum, nickel, chromium, iron, stainless, copper, etc.), paper which is rendered electrically conductive, as well as polymeric films and glass plates having an electrically conductive coat of the above metals, Au, Ag, indium oxide, indium tin oxide, etc.

A surface layer such as a protective layer and an insulating layer may further be provided on the photosensitive layer so as to prevent mechanical damage and chemical change in properties of the photosensitive layer. The protective layer is a layer having low electric resistance of $10^8$ to $10^{14}$ Ωcm which can be used in the so-called Carlson process, and the insulating layer is an electrically insulating layer which can be used in a process as described in U.S. Pat. Nos. 3,041,167 and 3,438,706. Both layers are substantially transparent to light for exposure and the thicknesses of the protective layer and the insulating layer are about 2 to 20 μm and about 10 to 40 μm, respectively.

In order to prevent injection of electrons from an electrically conductive support to the photosensitive layer, a barrier layer may be formed between the support and the photosensitive layer. For this purpose, aluminum oxide, nylon, and epoxy resins can be used. Such a barrier layer may not be formed when the photoreceptor is used in the process of U.S. Pat. Nos. 3,041,167 and 3,438,706 as described above or when the charge transport layer is formed as a lower layer on the support in the preparation of a double-layered photoreceptor (FIG. 2). An adhesive layer may also be formed between the support and the photosensitive layer to improve adhesion therebetween.

The electrophotographic photoreceptor of the present invention may be used not only with ordinary copiers but also with laser printers, as well as intelligent copiers since the photoreceptor of the present invention is sensitive to lasers. Lasers which can be applied to the photoreceptor of the present invention are preferably semiconductor lasers such as those of Ga-As type semiconductors (e.g., Ga-As, Al-Ga-As, Ga-As-P, etc.).

The electrophotographic photoreceptor of this invention can be widely used not only in a usual copying machine but also in a semiconductor laser printer and an intelligent copier.

The invention will now be explained in more detail by the following non-limiting examples.

EXAMPLE 1

Preparation of Compound (1)

In a mixture of 1-butanol and toluene, 12.74 g of N-methyl-N-(4-nitrobenzyl)aniline and 3.00 g of squaric acid were heated for 5 hours at 100° C. to 120° C. with stirring. After cooling, the greenish crystals precipitated were collected by filtration and washed with diethylether to give 2.10 g of the desired squarium compound. (yield: 14%)

Decomposition Point: 273.0° C.–274.0° C.

Infrared Absorption Spectrum (KBr Tablet): $\nu_{NO_2}$ 1615 cm$^{-1}$.

Visible Absorption Spectrum: $\lambda_{max}$ 628 nm (dichloromethane solution).

| | Elemental Analysis: | | |
|---|---|---|---|
| | C (%) | H (%) | N (%) |
| Found | 68.21 | 4.45 | 9.84 |
| Calc'd | 68.32 | 4.66 | 9.96 |

EXAMPLES 2 to 4

Preparation of Compound (2) to (4)

By using the corresponding aniline derivatives, Compounds (2) to (4) were prepared in the same manner as described in Example 1.

Compound (2)

Decomposition Point: 247.0° C.–248.0° C.,

Infrared Absorption Spectrum (KBr Tablet): $\nu_{C\equiv N}$ 2230 cm$^{-1}$.

Visible Absorption Spectrum: $\lambda_{max}$ 631 nm (dichloromethane solution).

| | Elemental Analysis: | | |
|---|---|---|---|
| | C (%) | H (%) | N (%) |
| Found | 78.31 | 4.89 | 10.65 |
| Calc'd | 78.14 | 5.01 | 10.71 |

Compound (3)

Decomposition Point: 308° C.

Infrared Absorption Spectrum (KBr Tablet): $\nu_{C=O}$ 1720 cm$^{-1}$, 1690 cm$^{-1}$.

|        | Elemental Analysis: | | |
|--------|---------------------|-----------|-----------|
|        | C (%)               | H (%)     | N (%)     |
| Found  | 72.71               | 5.21      | 4.93      |
| Calc'd | 72.84               | 5.03      | 5.00      |

Compound (4)

Decomposition Point: 245.0°-255° C.

Infrared Absorption Spectrum (KBr Tablet): $\nu_{C=O}$ 1720 cm$^{-1}$.

Visible Absorption Spectrum: $\lambda_{max}$ 630 nm (dichloromethane solution).

|        | Elemental Analysis: | | |
|--------|---------------------|-----------|-----------|
|        | C (%)               | H (%)     | N (%)     |
| Found  | 74.16               | 5.80      | 4.60      |
| Calc'd | 74.01               | 5.88      | 4.54      |

EXAMPLE 5

A squarium compound of this invention represented by the general formula (I) wherein X is a nitro group (i.e., Compound (1)) was ground with methylene chloride and steel balls for 12 hours. After grinding, the ground compound was added to a polyester resin (trade name: Vylon 200) in an amount of 30% by weight based on the weight of the polyester resin and mixed, and then the resulting mixture was coated using an applicator on an aluminum plate to prepare a charge generation layer having a dry thickness of about 0.5 μm. On this layer a composition composed of a polycarbonate resin (trade name: Panlite) and 50% by weight of 1-phenyl-3-(p-diethylaminostyryl)-5-(p-diethylaminophenyl)pyrazoline based on the weight of the composition was coated using an applicator to prepare a transport layer having a thickness of about 15 μm.

The photosensitive surface of this photoreceptor was charged negative by corona discharge of −6 KV for 2 seconds using an electrostatic copy paper test instrument manufactured by Kawaguchi Denki Co., Ltd. After it was allowed to stand for 2 seconds in the dark, its surface potential ($V_0$) was measured and then a light from a tungsten-halogen lamp having an illuminance of 10 luxes was irradiated to the photosensitive layer. The time when the value of the surface potential charged to half the original value was determined to obtain a half exposure value ($E_{\frac{1}{2}}$).

As a result, $V_0$ was 720 V and $E_{\frac{1}{2}}$ was 2.0 lux·second.

EXAMPLE 6

Electrophotographic photoreceptor was prepared in the same manner as described in Example 5 except that the squarium compound wherein X is a cyano group (i.e., Compound (2)) was used in place of the squarium compound used in Example 5, and their electric characteristics were measured.

As a result, $V_0$ was 630 V and $E_{\frac{1}{2}}$ was 4.9 lux·second.

Examples 7 and 8

Electrophotographic photoreceptors with inverted order of the charge generation layer and the charge transport layer were prepared. That is, the procedures in Examples 5 and 6 using squarium Compounds (1) and (2), respectively were repeated except that the order of the charge generation layer and the charge transport layer was inverted. Their electric characteristics of the resulting photoreceptors were measured. The results obtained are shown in Table 1.

TABLE 1

| Example | Compound No. | $V_0$ (V) | $E_{\frac{1}{2}}$ (lux · sec) |
|---------|--------------|-----------|-------------------------------|
| 7       | (1)          | 700       | 2.1                           |
| 8       | (2)          | 610       | 5.2                           |

While the invention has been described in detail and with reference to specific embodiments thereof, it will be apparent to one skilled in the art that various changes and modifications can be made therein without departing from the spirit and scope thereof.

What is claimed is:

1. A squarium compound represented by formula (I):

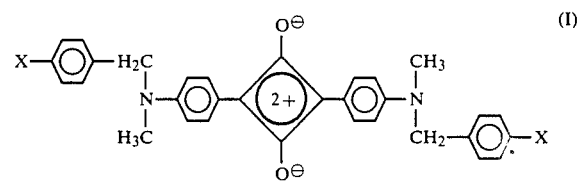

wherein X represents a nitro group, a cyano group, a carboxyl group or an ethoxycarbonyl group.

* * * * *